US00PP22298P3

(12) United States Plant Patent
Jackson et al.

(10) Patent No.: US PP22,298 P3
(45) Date of Patent: Dec. 6, 2011

(54) EASTERN REDBUD TREE NAMED 'JN3'

(50) Latin Name: *Cercis canadensis*
Varietal Denomination: JN3

(76) Inventors: Ray Jackson, Belvidere, TN (US); Cindy Jackson, Belvidere, TN (US)

( * ) Notice: Subject to any disclaimer, the term of this patent is extended or adjusted under 35 U.S.C. 154(b) by 88 days.

(21) Appl. No.: 12/460,803

(22) Filed: Jul. 24, 2009

(65) Prior Publication Data

US 2011/0023196 P1 Jan. 27, 2011

(51) Int. Cl.
*A01H 5/00* (2006.01)

(52) U.S. Cl. ..... Plt./216

(58) Field of Classification Search ..... Plt./216
See application file for complete search history.

(56) References Cited

U.S. PATENT DOCUMENTS

| | | | |
|---|---|---|---|
| PP10,328 | P | 4/1998 | Covey |
| PP15,854 | P2 | 7/2005 | Woody |
| PP17,161 | P3 | 10/2006 | Woody |
| PP19,654 | P2 | 1/2009 | Swanson et al. |

*Primary Examiner* — Kent L Bell
(74) *Attorney, Agent, or Firm* — Polster, Lieder, Woodruff & Lucchesi, LC

(57) ABSTRACT

An Eastern Redbud tree named 'JN3' having golden orange new growth and specked lime green mature foliage with a wavy, rugose dark green margin and also capable of being reproduced reliably from chip budding.

4 Drawing Sheets

CROSS-REFERENCE TO RELATED APPLICATIONS

U.S. Plant Pat. No. 21,451 for an Eastern Redbud Tree named 'JN2'.

STATEMENT REGARDING FEDERALLY SPONSORED RESEARCH

Not Applicable.

BACKGROUND OF THE INVENTION

The present invention relates to a new and distinct variety of *Cercis canadensis*, Eastern Redbud, referred to by its varietal name 'JN3'.

Discovery

I discovered my new tree in the spring, 2008, growing in a production area of a liner production field in Belvidere, Franklin County, Tenn., among a group of cultivated *Cercis canadensis* 'JN2' The Rising Sun™. My *Cercis canadensis* 'JN2' Eastern Redbud tree is the subject of U.S. Plant Pat. No. 21,451. My new Eastern Redbud tree 'JN3' appeared as a branch sport of a bare root liner which had been budded in the summer, 2006.

Propagation

'JN3' was asexually propagated at my direction in the Summer, 2007 by chip budding onto seedling rootstock. This took place at my nursery in Belvidere, Tenn. The propagation and resulting progeny have demonstrated that the characteristics of my new tree are firmly fixed. Observations have confirmed that my new tree represents a new an improved variety of the Eastern Redbud tree as evidenced by its speckled lime green mature foliage with a wavy, rugose dark green leaf margin, and that my Eastern Redbud tree 'JN3' can be reliably asexually propagated. My tree is 4 years old, approximately 6' tall with a diameter of approximately 1½ inches at a height of 1 inch above the ground. The current tree height and diameter are typical of the species for a 4 year old tree.

Uniqueness

My Eastern Redbud tree 'JN3' was observed to have the same color golden orange new growth and speckled lime green mature foliage as my Eastern Redbud tree 'JN2' but with a wavy, rugose dark green leaf margin. These characteristics distinguish my new tree from other typical seedling Eastern Redbud trees and known cultivars.

Use

My Eastern Redbud tree 'JN3' has been observed for a period of time and is believed to be particularly useful as a specimen tree or accent plant, or for use in groupings for a lawn or shrub border. An Eastern Redbud tree with golden orange new growth and speckled lime green mature foliage, contrasted by a dark green marginal variegation, and having a wavy, textured leaf would be very striking in a landscape setting.

BRIEF SUMMARY OF THE INVENTION

Background

The Eastern Redbud tree is typically a small tree with pink flowers in the spring and flat green foliage in summer with spreading branches forming a rounded canopy. My new cultivator differs from the species in that it has a golden orange new growth and specked lime green mature foliage with a wavy, rugose dark green margin. The range of the Eastern Redbud tree extends from northern Florida to New Jersey, and west to Missouri, Texas, and northern Mexico. It is found in a variety of climates ranging from wet to dry and in a variety of soils ranging from alkaline to acidic. It is considered an understory tree and is very tolerant of nutrient competition and shade.

Industry Representation

A cultivated Eastern Redbud tree is represented in the industry by seedling material and several cultivars. Most redbud trees are grown from seed, but there are a number of popular and available cultivars which are propagated by budding or tissue culture. In his *Manual of Woody Landscape Plants,* Dr. Michael A. Dirr lists 12 cultivars of *Cercis canadensis,* 2 subspecies, and 2 cultivars of the subspecies *texensis*. Although this list is not exhaustive, it does represent what was generally available to the industry prior to 1998. None of these cultivars has the golden orange foliage color of my new tree, which, when mature, has a speckled lime green foliage with a wavy, rugose dark green margin. My Eastern Redbud tree 'JN2' which is the subject of U.S. Plant Pat. No. 21,451 does not exhibit foliage with a wavy, rugose dark green margin or edging.

A search of the United States Patent and Trademark Office published patents shows 6 patented cultivars, 4 of which do not appear on Dr. Dirr's list. Only one of these, *Cercis canadensis* 'Hearts of Gold' U.S. Plant Pat. No. 17,740 (referred to hereinafter as 'Hearts of Gold') has a yellow foliage color. Although there is no industry data on redbud sales, the most popular cultivar of *Cercis canadensis* at the current time is probably *Cercis canadensis* 'Forest Pansy' (not patented), which has a purple leaf. The 'Hearts of Gold' tree has only recently been available to the industry, but it is gaining in popularity. It is described in U.S. Plant Pat. No. 17,740 as having an "orange-red" new growth, "bright, yellow-green leaves," and "bright golden foliage". My new Eastern Redbud tree has a golden orange new growth and speckled lime-green mature leaves with a wavy, rugose dark green margin. In the summer, 2007, a severe drought in our area (middle Tennessee) provided an opportunity to observe the durability of these two cultivars side-by-side. 'The Hearts of Gold' redbud tree quit flourishing in late summer and its foliage faded to a pale yellow green and burned in the heat and drought. My 'JN2' redbud tree previously referred to continued to flourish through the summer, producing new golden orange foliage that did not burn. I expect my new Eastern Redbud tree 'JN3' to exhibit a similar hardiness. A late freeze in the spring, 2007, killed back many of the propagules of my tree 'JN2', as well as other seedling and cultivars. As a result, the largest specimen of my 'JN3' Eastern Redbud tree is currently about 4' tall and ¼" in caliper.

BRIEF DESCRIPTION OF THE SEVERAL VIEWS OF THE DRAWINGS

The accompanying photographs depict the color of the tree and foliage of my new variety as nearly as is reasonably possible to make the same in a color illustration of this character.

The first photograph depicts the development of the new growth of my 'JN3' Eastern Redbud tree. The newest growth is golden orange (RHS 23B), developing into bright yellow (RHS 6C), and then into yellow green (RHS 151D).

The second photograph depicts the full development of the tree's foliage from new to mature. The newest growth is golden orange (RHS 23B), developing into bright yellow (RHS 6C), then into yellow green (RHS 151D), and finally maturing into light green (RHS 139B) with some lighter and darker speckling.

The third photograph depicts the speckling which appears as the leaf matures and is best represented as green (RHS 141B) on a yellow green (RHS 153A) background.

The fourth photograph depicts a comparison between my 'JN3' redbud tree (the two trees on the right) and a cutting of 'Hearts of Gold' on the left. The slightly pendulous habit can be seen on the new growth of my 'JN3' redbud tree in contrast to the less pendulous growth of the 'Hearts of Gold' redbud tree. This figure also shows the contrast of the "orange red" new growth of the 'Hearts of Gold' tree and the golden orange new growth of my new Eastern Redbud tree 'JN3'.

DESCRIPTION OF THE PREFERRED EMBODIMENT

The following is a detailed description of my new variety of eastern Redbud with color terminology in accordance with The Royal Horticultural Society (R.H.S.) colour chart except where the context indicates a term having its ordinary dictionary meaning. My new tree has not been observed under all growing conditions and variations may occur as a result of different growing conditions. All progeny of my new variety of redbud tree, insofar as have been observed, have been identical in all the characteristics described below.

Other than as set forth below, as of this time, no other characteristics of my new 'JN3' redbud tree have been observed by the inventor which are different from the characteristics common to Eastern Redbud trees.

Parentage: Branch sport of a bare root liner which had been budded in the summer, 2006.

Locality where grown and observed: A production field in Belvidere, Franklin County, Tenn.

Leaves: Slightly larger than is typical of the species, but insignificantly so; opposite, simple, broad-ovate to suborbicular, cordate, acute, entire, 4" to 6" wide by 4" to 6" long. The leaf color, on both the upper and lower surfaces of the leaf, develops from a golden orange to a speckled lime green as shown in the first and second photographs. The new growth is golden orange (RHS 23B), developing into bright yellow (RHS 6C), then into yellow green (RHS 151D). The speckling appears as the leaf matures, as shown in the third photograph, and is the best represented as green (RHS 141 B) on a yellow green (RHS 153A) background. At maturity, as shown by the lower leaves in the second photograph, the leaves are light green (RHS 139B) with some lighter and darker speckling. Fall color is typical of the species, light yellow (RHS 7A).

Petiole: Typical of the species; 1½' to 2½' long, 3/16"-¼" in diameter, emerging orange (RHS 53D) to pink (RHS 50B) and maturing to light green (RHS 153D). The first, second, and third photographs show this trait.

Buds: Typical of the species; absent terminal buds; small laterals ⅛" or less long, blunt, blackish red (RHS 185A), somewhat flattened and appressed, overlapping bud scales, and somewhat hairy on the edges. Flower buds are larger and more rounded than leaf buds and are often clustered around each node. The flower buds are erect, inverted conical, 2-3 mm long, 1-1.4 mm wide basally expanding to 2.4-3.5 mm apically; swelling in mostly late March in clusters of 4-8.

Flowers: Typical of the species; perfect, reddish-purple (RHS 63A) in bud opening to a pinkish-purple bloom (RHS 66C); ½" long on a ½" pedicel; flower in March-April for 2-3 weeks; fascicled or racemose, borne 4"-8" together, often flowering on old trunks 4"-8" in diameter. The species typically flowers in 4-6 years from a seed. My new tree has already flowered after 3 years of observation, as shown in the fourth photograph. The shape of the flower is pea-like (papilionaceous) pedicillateis light pinkish (RHS 65D). Calyx-broad campanulate pinkish-purple (RHS 66C); tube ten (10) veined 1 mm long by 3 mm wide. The margin is entire. The apex is tapering to an acute or infrequently subacuminate, mucronate. The base is cordate. Broad ovate lobes, obtuse 1-2 mm long by 1-1.5 mm wide, shriveling upon maturation. The diameter of a flower, if laid flat, is ½" to 1'. The flower has five (5) petals, papilionaceous; two (2) keel petals enclosing reproductive organs, blade shaped, 5 mm long, 2 mm wide, claw 2 mm; two (2) wing petals, ascending, blade oblong, 3 mm long, 2 mm wide, claw 2.2-2.5 mm; and one (1) banner petal, 4 mm long, 3 mm wide, claw 2 mm. The claws all lack pigmentation. Stamens: ten (10), distinct, free, filaments 4 mm long, anthers 0.5 mm. Pistil: one (1), exceeding stamens slightly; ovary is 3.5 mm long. Style: 1.8-2 mm long, curving, some elliptically; stigma, capitate, 3 mm diameter. Bracts are scale like, imbricated, appressed, flabellate, obtuse, cilolate, 0.6-1.0 mm long and 1-1.5 mm wide. Pedicels are less than 1 mm in length and diameter, and a yellow (RHS 11C) color.

Fruit: I have not yet observed fruit on my new tree.

Stem: Slender, 3 inches to 6 inches in length with a diameter of ⅛ inch to 3⁄16 inches, glabrous, similar to the petioles in color: initially light yellow (RHS 11A), maturing to light green (RHS 153D)) in the first year and then brown (RHS 199A) in the second year. The first, second, and third photographs also show this trait.

Trunk: Lighter in color than the species, but not significantly so. The species has a bark that matures to brownish-black and develops a scaly condition. My new 'JN3' redbud tree currently has a golden brown (RHS N199D) mature bark, and has a diameter of 11½ inches measured 1 inch above the ground.

Branching: Typical of the species with ascending, spreading branches. Both the new growth and mature stems are somewhat pendulous compared to the 'Hearts of Gold' redbud tree, which is described as having "upright stems and primary branches." This trait and comparison between the trees is shown in the fourth photograph. The branches of my new Eastern Redbud tree 'JN3' are 2'-4' long and have a diameter of 3⁄16" and has a light yellow color (RHS 11C).

Root System: Redbuds are difficult to propagate from cuttings and all of the propagules of my new 'JN3' redbud tree have been reproduced from chip budding onto seedling rootstocks. If it does become possible to reproduce my new tree from rooted cuttings or from tissue culture, I expect the root system to be typical of the species, which is medium to coarse.

Growth habit: Typical of the species which is 7'-10' in the first 5-6 years; small, spreading tree with moderate growth rate. My new tree 'JN3' is approximately 6' tall with a diameter of approximately 1½ inches at a height of 1 inch above the ground.

Vigor: More vigorous than the species; performs well in heat and drought.

Diseases: The species is susceptible to canker, verticillium wilt, and leaf spot. I have not observed any of these on my new tree or its propagules.

Pests: Treehoppers, leafhoppers, caterpillars, and scales can all cause damage, but the damage is cosmetic and rare. Eastern Redbud trees as a species are resilient to pests. I have observed no pest problems on my new tree or its propagules.

I claim:

1. A new and distinct variety of Eastern Redbud tree named 'JN3' substantially as herein shown and described, characterized particularly as to novelty by its golden orange new growth and speckled lime green mature foliage with a wavy, rugose dark green margin.

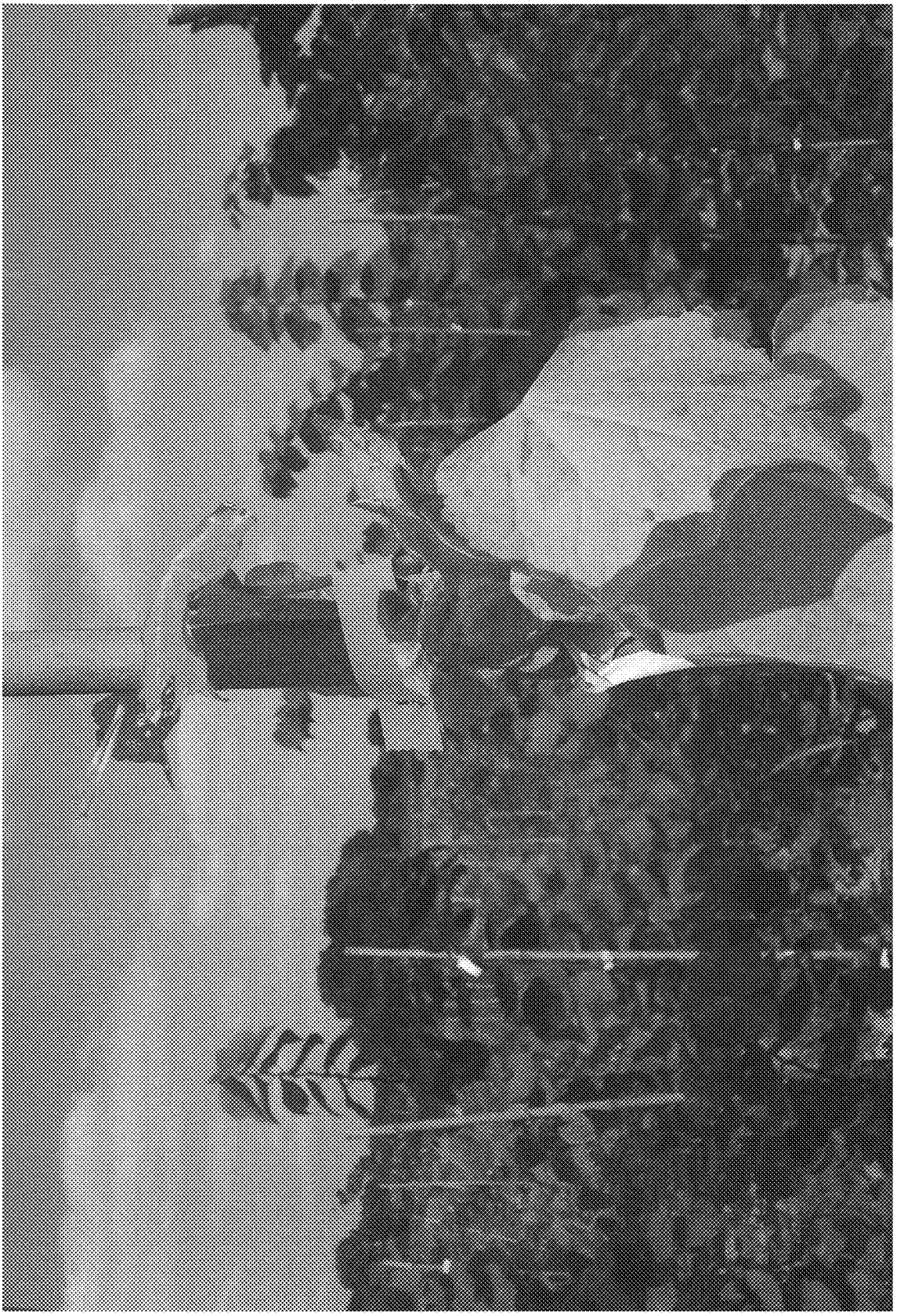

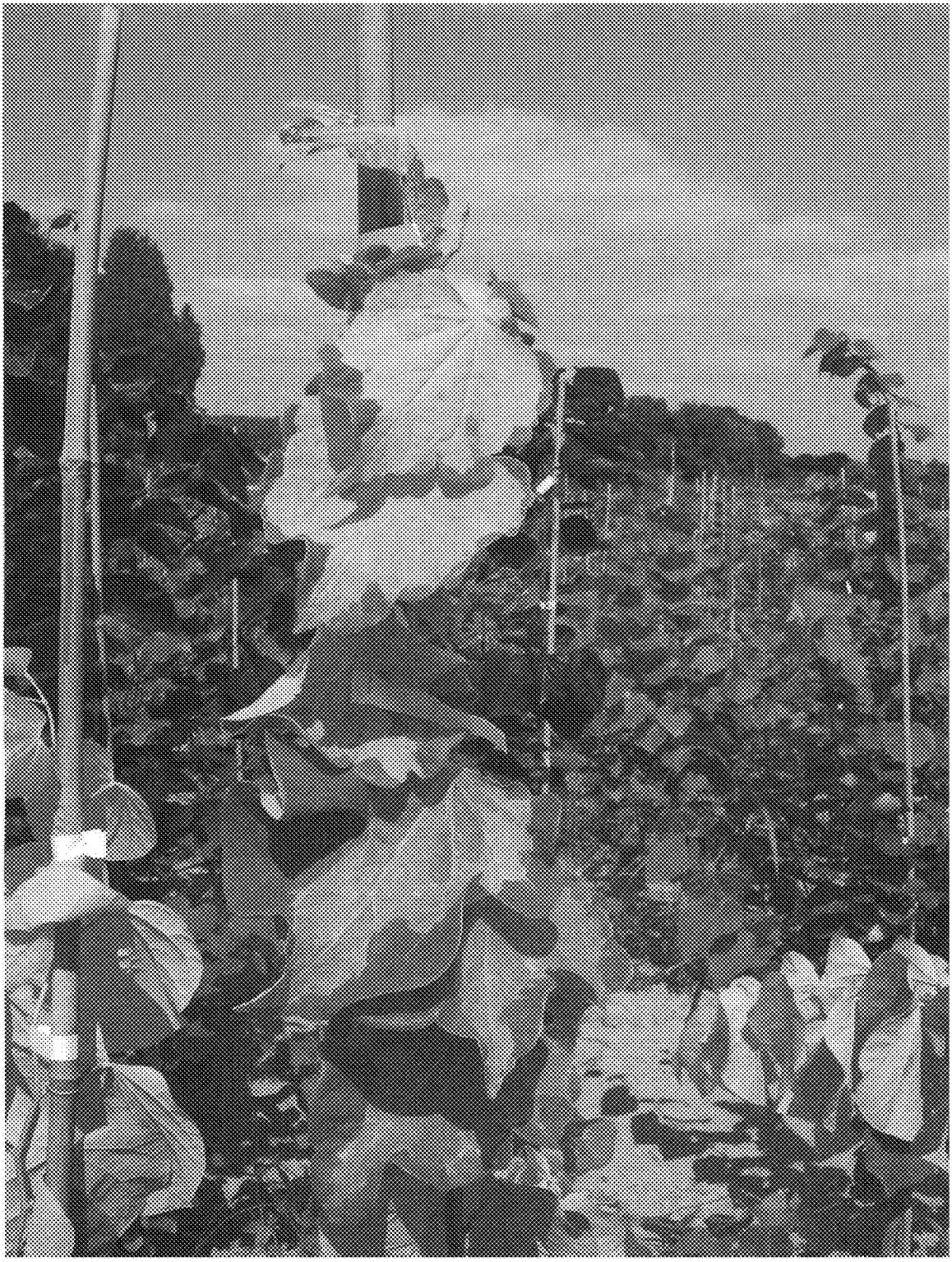

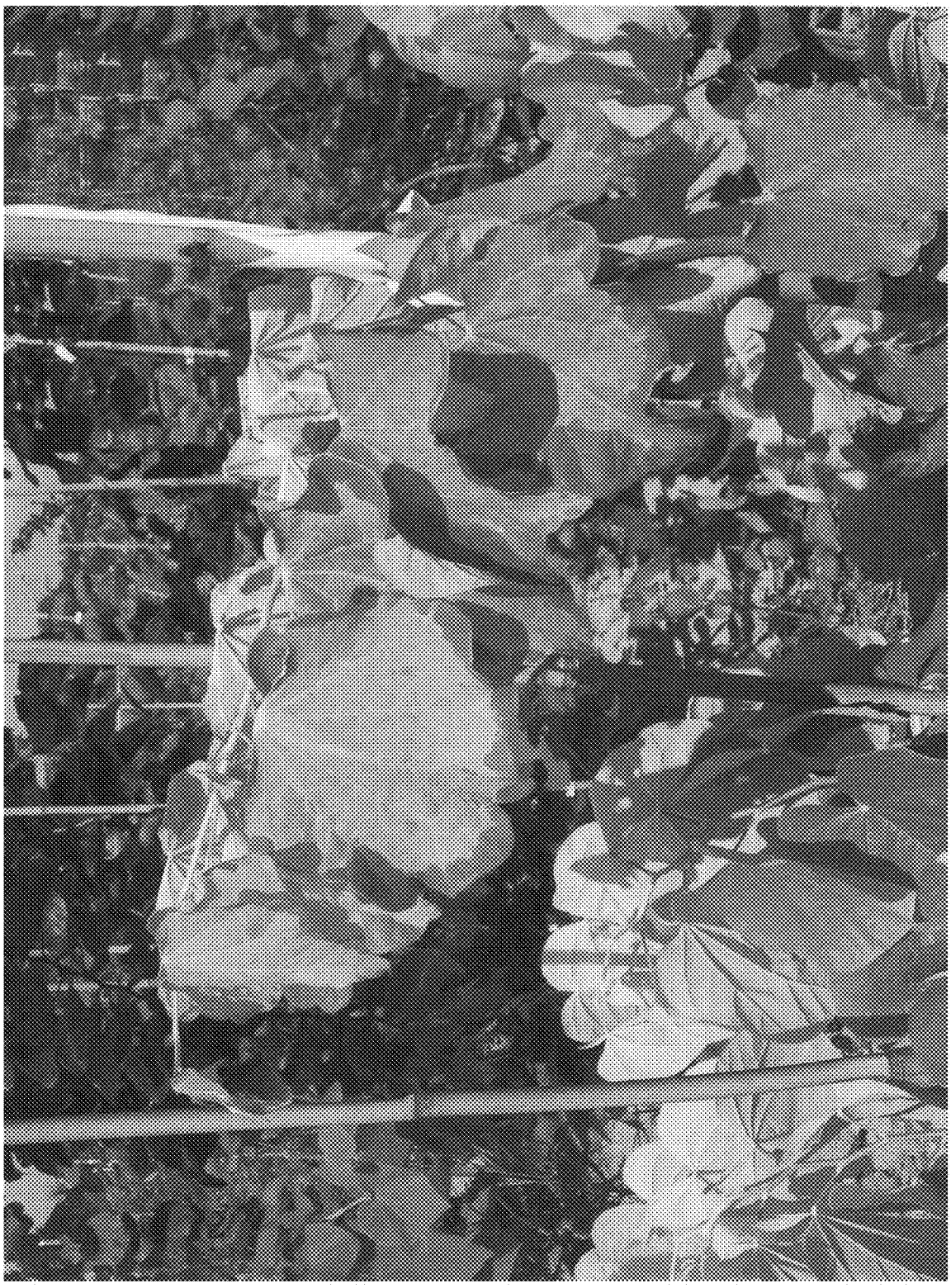

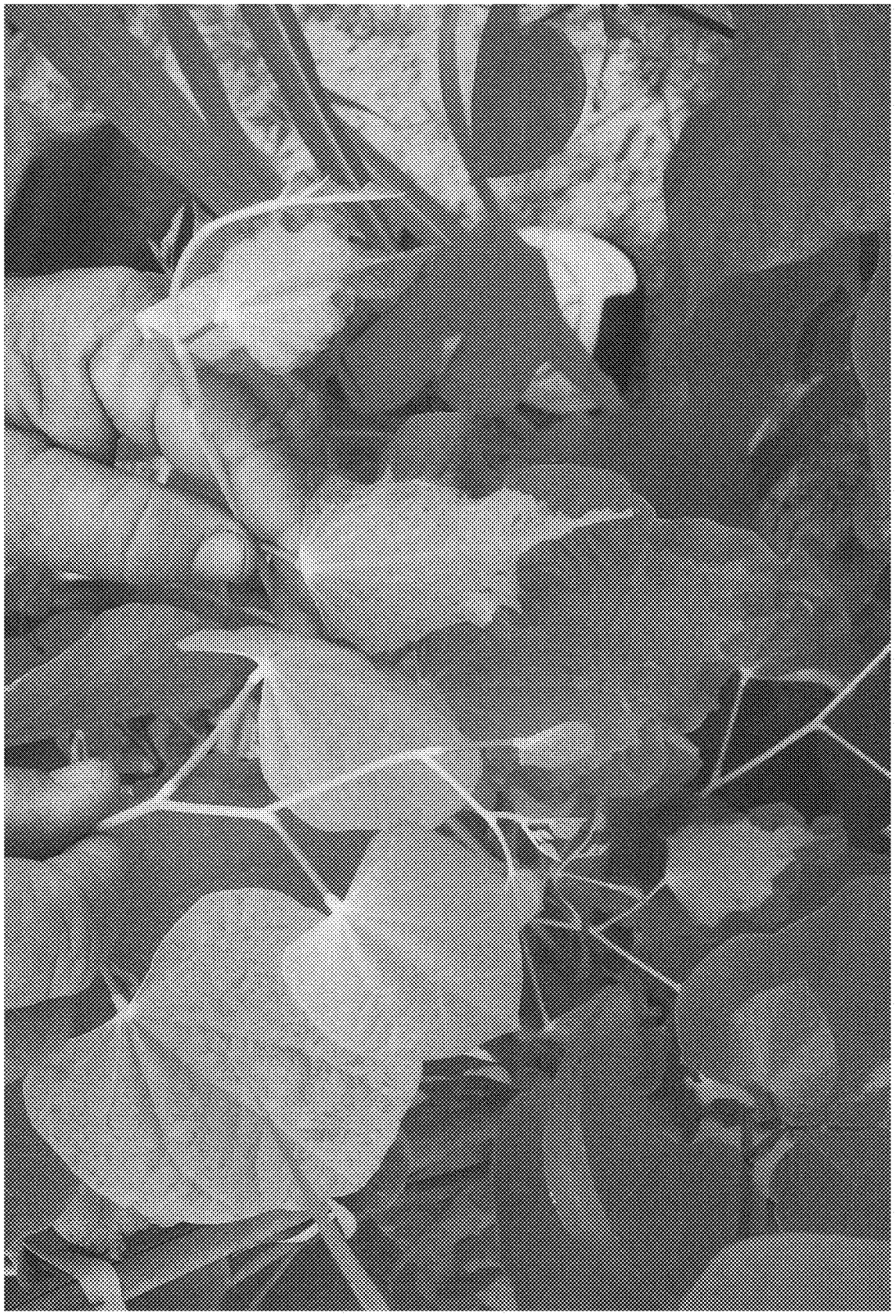

* * * * *